United States Patent [19]

Enomoto et al.

[11] 4,416,269

[45] Nov. 22, 1983

[54] APPARATUS FOR VIBRATING THE ULNA IN VIVO

[75] Inventors: Shogo Enomoto, Tokorozawa; Masanobu Sawai, Yamato; Iwao Seo; Tomonobu Yamaguchi, both of Ami, all of Japan

[73] Assignees: Teikoku Hormone Mfg. Co. Ltd.; Mitsubishi Petrochemical Co., Ltd., both of Tokyo, Japan

[21] Appl. No.: 281,045

[22] Filed: Jul. 7, 1981

[30] Foreign Application Priority Data

Jul. 11, 1980 [JP] Japan .................................. 55-93826

[51] Int. Cl.[3] .............................................. A61M 1/00
[52] U.S. Cl. ...................................... 128/41; 128/51; 128/739
[58] Field of Search ...................... 128/41, 51, 52, 53, 128/660, 739, 773, 786, 782; 248/124, 125; 73/634

[56] References Cited

U.S. PATENT DOCUMENTS

| | | | |
|---|---|---|---|
| 2,668,912 | 2/1954 | Goldfield et al. | 248/124 |
| 3,477,422 | 11/1969 | Jurist, Jr. et al. | 128/2 |
| 4,226,390 | 10/1980 | Steggall | 248/124 |

OTHER PUBLICATIONS

John M. Jurist, Ph.D., In Vivo Determination of the Elastic Response of Bone I. Method of Ulnar Resonant Frequency Determination, Phys. Med. Biol., 1970, vol. 15, No. 3, 417–426.

John M. Jurist, Ph.D., In Vivo Determination of the Elastic Response of Bone II. Ulnar Resonant Frequency in Osteoporotic, Diabetic and Normal Subjects, Phys. Med. Biol., 1979, vol. 15, No. 3, 427–434.

Kurt F. Konkel, MD. et al., Tibial Resonant Frequency in Paget's Disease, Wisconsin Medical Journal, May 1973, vol. 72, 123 and 124.

Primary Examiner—Richard J. Apley
Assistant Examiner—J. L. Kruter
Attorney, Agent, or Firm—Wenderoth, Lind & Ponack

[57] ABSTRACT

An apparatus for vibrating the ulna in vivo includes a main post provided upright on a base stand, and a horizontally extending upper arm secured to the upper part of the main post for vertical movement. The apparatus also includes a plate for fixing the back of the hand; the plate is secured to the end of the upper arm for free movement at an arbitrary angle of inclination. A lower arm which is secured for vertical movement to the lower part of the main post and extending in the same horizontal direction as the upper arm is also provided. In addition, an excitor is mounted on the lower arm for sliding movement in the axial direction of the lower arm and in a horizontal direction perpendicular thereto, and a brachium resting plate is fixed ahead of the excitor.

8 Claims, 8 Drawing Figures

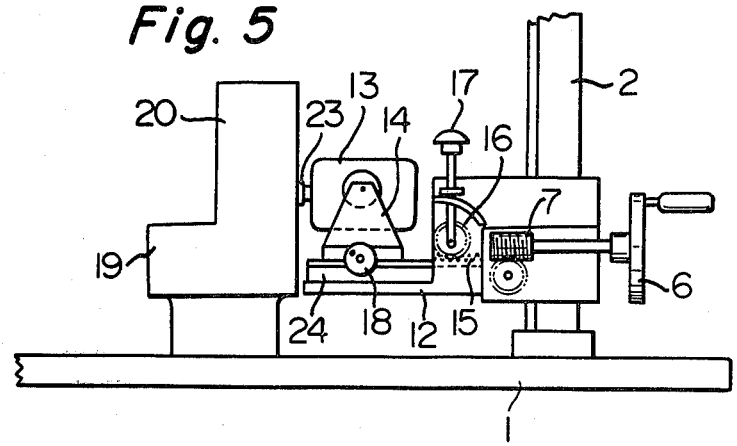
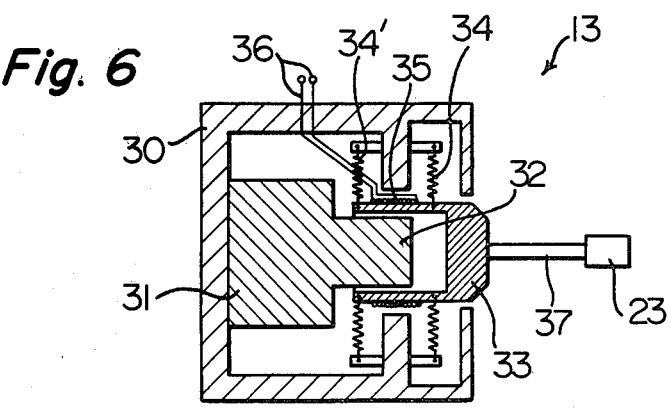
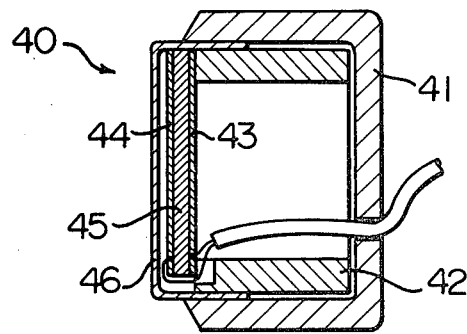

APPARATUS FOR VIBRATING THE ULNA IN VIVO

BACKGROUND OF THE INVENTION

This invention relates to an apparatus for vibrating the ulna *in vivo*, and more specifically, to an apparatus for externally vibrating the ulna *in vivo* which is useful for measuring the resonant frequency of the ulna *in vivo* by imparting vibratory motion to it externally and examining the dynamical properties of the bone from the resonant frequency measured.

About 1970 Jurist and other workers pioneered a method for measuring the resonant frequency of the ulna or tibia *in vivo* by externally applying to it a vibratory motion having a frequency of 100 to 1,000 Hz and examining the dynamic properties of the bones from the resonant frequency measured. They point out that the product FL of the resonant frequency F of the ulna and the ulnar length L in patients with osteoporosis, diabetes, etc. evidently differs from FL in normal healthy persons [J. M. Jurist, "Phy, Med. Biol.," 15, 417 (1970); J. M. Jurist, "Phy. Med. Biol.," 15, 427 (1970); and K. F. Konkel & J. M. Jurist, "Wis. Med. J.," 72, 123 (1973)]. Some apparatuses for measuring such resonant frequencies F have also been proposed [see, for example, U.S. Pat. No. 3,477,422 to J. M. Jurist, and Japanese Laid-Open Patent Publication No. 111,484/1974].

It is, however, difficult to measure the inherent resonant frequency of a bone *in vivo* while minimizing interferences by other bones, muscles, etc., and according to the apparatuses proposed heretofore, it is difficult to measure resonant frequencies accurately with good reproducibility.

The present inventors made extensive investigations about a method for measuring the resonant frequency of a living bone of a forearm, especially the ulna, and found that the resonant frequency of the ulna considerably varies with the direction of the hand and this is because the supination and pronation of the forearm exert different effects on the force acting on the bone through the ligament. These investigations have finally led to the discovery that the reasonant frequency of the ulna can be measured accurately if vibratory motion is imparted to the elbow in such a way as to minimize any external force on the bone and to allow the ulna to vibrate freely in the transverse direction while its both ends are kept free.

SUMMARY OF THE INVENTION

Thus, according to this invention, there is provided an apparatus for vibrating the ulna *in vivo*, comprising:
a base stand,
a main post provided upright on the base stand,
a horizontally extending upper arm secured to the upper part of the main post for vertical movement,
a plate for fixing the back of the hand, said plate being secured to the end of the upper arm for free movement at an arbitrary angle of inclination,
a lower arm secured for vertical movement to the lower part of the main post and extending in the same horizontal direction as the upper arm,
an exciter mounted on the lower arm for sliding movement in the axial direction of the lower arm and in a horizontal direction perpendicular thereto, and
a brachium resting plate fixed in front of the excitor.

The apparatus of the present invention is described in more detail below with reference to the accompanying drawings showing the preferred embodiments of the invention.

BRIEF DESCRIPTION OF THE DRAWINGS

In the accompanying drawings,
FIG. 5 is a side elevation of a part of the vibrating apparatus of the invention in another embodiment;
FIG. 6 is a sectional view of the excitor used in the apparatus of the invention;
FIG. 7 is a sectional view of a transducer provided in contact with the capitulum ulnae part of the wrist when measuring the resonant frequency of the ulna by the vibrating apparatus of the invention.

DESCRIPTION OF THE PREFERRED EMBODIMENTS

Figure 1:
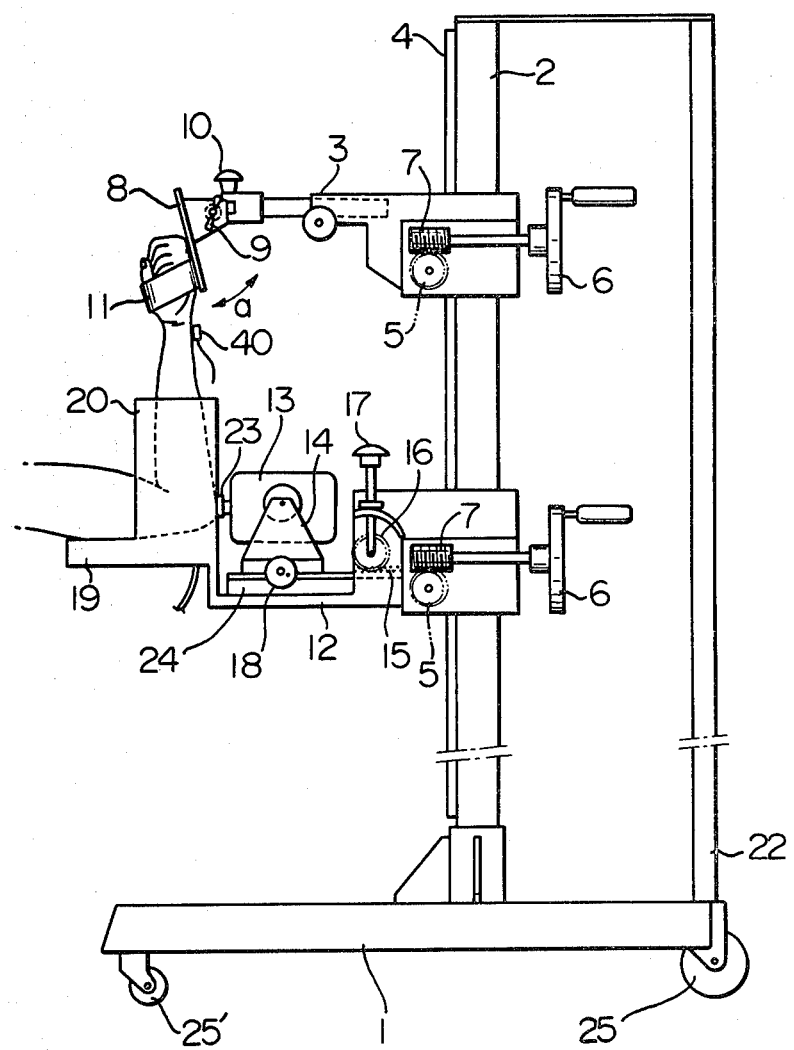
FIG. 1 is a side elevation of the vibrating apparatus of the invention.
Figure 2:
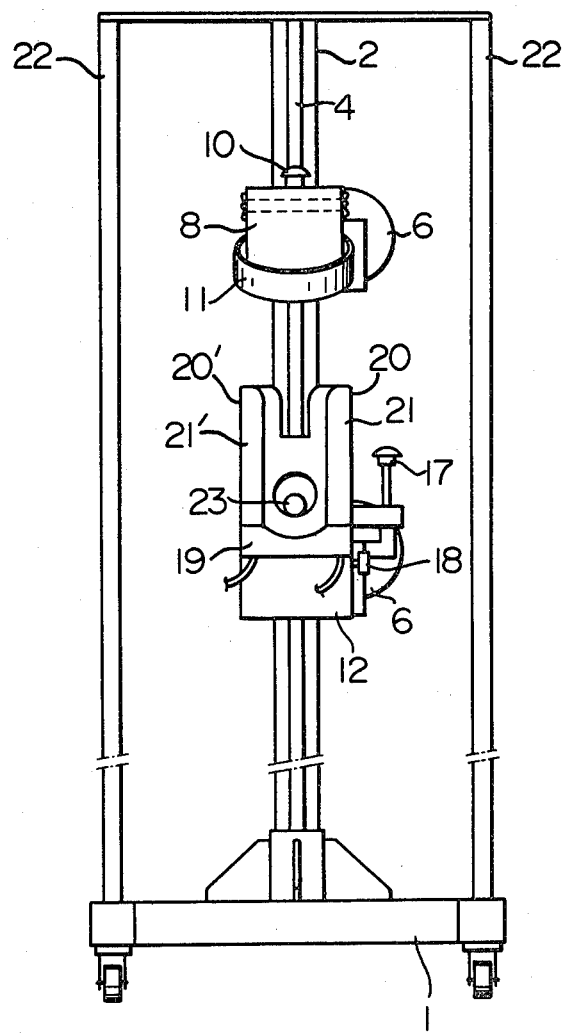
FIG. 2 is a front elevation of the apparatus shown in FIG. 1.
Figure 3:
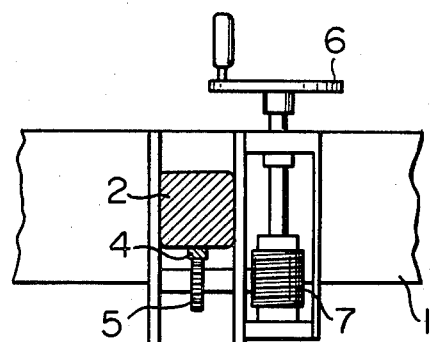
FIG. 3 is a top plan view of the upper arm of the above apparatus.
Figure 4:
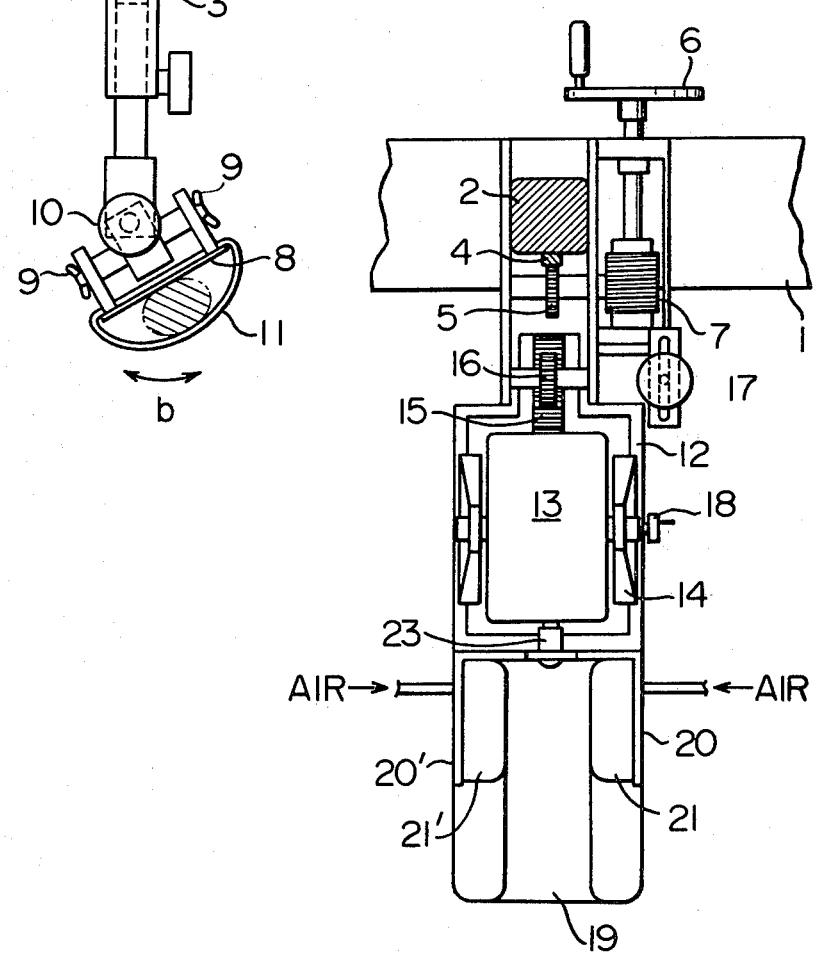
FIG. 4 is a top plan view of the lower arm of the above apparatus.

Referring to FIGS. 1 to 4, a main post 2 is provided nearly perpendicular to and on a base stand 1. As required, castors 25 and 25' may be secured to the base stand 1 to make it easier to move. There is no particular restriction on the height of the main post provided upright on the stand 1, but it may usually be about 50 to about 200 cm. To the upper part of the main post 2 is secured a horizontally extending upper arm 3 for vertical movement. Mounting of the upper arm 3 in this state may be effected by any known means. For example, as shown in FIG. 1, a rack 4 may be fixed longitudinally to a suitable part of the main post 2 and brought into engagement with a pinion 5 fixed to the upper arm 3. The pinion 5, as shown in FIG. 3, is connected to a handle 6 through a worm gear 7.

A plate 8 for fixing the back of the hand is secured to the forward end of the upper arm 3. It is set at an arbitrary angle of inclination to the upper arm. For example, the plate 8 is secured to the forward end of the upper arm 3 in such a manner that it can rotate through half a turn in the direction of arrow a in FIG. 1 or in the direction of arrow b in FIG. 3. The plate 8 can be secured to the upper arm 3 at a desired angle of inclination of the axis of the upper arm by suitably combining and adjusting screw members 9 and 10.

To the plate 8 is fixed a band member 11 which can be used to hold the hand onto the fixing plate 8 so as to bring the back of the hand into the closest possible contact with the surface of the fixing plate 8 (see FIG. 1).

If desired, the upper arm 3 may be built in a telescopically stretchable structure as shown in FIG. 1.

On the other hand, a lower arm 12 is secured vertically movably to the lower portion of the main post 2. Mounting of the lower arm 12 can be effected in the same way as in the case of the upper arm 3.

An excitor 13 for imparting vibratory motion to the ulna is fixed to a suitable position of the lower arm 12. For example, as shown in FIG. 1, the excitor 13 may be fixed to a frame 14 provided in such a manner as to be horizontally slidable in a direction (to be sometimes referred to as the "left-and-right direction" in the present specification at right angles to the axial direction of the lower arm 12. In one embodiment, the excitor 13 may be supported by a shaft secured to the frame 14 so that the excitor 13 can be turned up and down.

The frame 14 is provided on a second frame 24 which is fixed slidably in the back-and-forth direction (i.e., the axial direction of the lower arm) on a track (channel or rail) provided on the lower arm 12. Horizontal sliding of the frame 14 in the left-and-right direction can be effected in a customary manner, for example by a screw mechanism composed of a male screw (not shown) connected to a handle 18 and a female screw (not shown) threaded in the frame 24.

The frame 24 is connected to a rack 15, and by operating both a pinion 16 kept in mesh with the rack 15 and a lever 17, the excitor 13 can be moved back and forth horizontally along the longitudinal direction of the lower arm 12.

A plate 19 for resting the brachium thereon is fixed in front of the excitor 13 on the lower arm 12 (i.e., on that side which is opposite to the main post). As shown in FIG. 2, the upper side surface of the plate 19 is desirably formed in concavity so as to maintain the brachium stable. At least the upper surface portion of the brachium resting plate is preferably made of a soft material such as flexible polyurethane foam.

As required, guide plates 20 and 20' as shown in FIG. 2 may be provided upright on both sides of the brachium resting plate 19 as antebrachium holding means, and inwardly of the guide plates 20 and 20' air bags 21 and 21' may be provided. The amount of air forced into the air bags may be adjusted by providing an air pump (not shown). This facilitates the positioning of the arm on the plate 19 and maintains the antebrachium stable.

In addition to the main post 2, an auxiliary post 22 may be provided upright on the base stand 1 to reinforce the main post 2.

A typical embodiment of the apparatus of this invention has been described hereinabove. As one modification, it is possible, as shown in FIG. 5, to fix the brachium resting plate 19 directly to the base stand 1. In FIG. 5, the upper arm portion is omitted because it is similar to that shown in FIGS. 1 and 3. The apparatus of the invention in accordance with the embodiment shown in FIG. 5 can be built in a portable structure, and is thus convenient for diagnosing a patient at a desk or bedside.

The excitor that can be used in this invention may be of any type which can produce frequencies and outputs sufficient for inducing the resonant phenomenon of the ulna *in vivo*. Generally, an electromagnetic excitor of the type shown in FIG. 6 is suitable.

In FIG. 6, a permanent magnet 31 is fixed to a casing 30 of the excitor 13, and a coil frame 33 made of an electrical insulating material is provided surrounding a projecting portion 32 of the permanent magnet 31. The coil frame 33 is held suspended within the casing 30 by spring members 34 and 34'. An electromagnetic coil 35 is wound around the coil frame 33. When a sine-wave current is caused to flow in the coil 35 through a conductor 36, the coil frame 33 vibrates as a result of the interaction between the permanent magnet 31 and the electromagnetic coil 35. As shown, a rod 37 projecting from a hole of the casing 30 is fixed to the coil frame, and a head 23 is secured fixedly to the end of the rod.

The amplitude and output of vibration of the coil frame 33 are determined by an electrical signal applied to the electromagnetic coil 35 and the spring constant of the spring members.

If the vibratory motion to be imposed into the bone through the head 23 of the excitor 13 is too vigorous, it causes great displacement of the bone so that the free-free transverse vibration of the bone is restricted. It also imparts discomfort or pain to the subject, and depending upon the condition of the bones of the subject, it is likely to result in bone damage. For practical purposes, therefore, it is generally advantageous that the excitor used in this invention exhibits the following performance.

Stroke: 23 1 mm, preferably 0.5 mm
Force rating factor: 0.5–20 kgf, preferably 1–10 kgf
Flexure stiffness: 0.5–10 kg/cm, preferably 1–5 kg/cm In imposing vibratory motion into the ulna *in vivo*, the apparatus of the invention is juxtaposed with the subject. The position of the lower arm 12 is then adjusted to nearly the same height as the height of the shoulder of the subject. The brachium is then rested on the plate 19 so that the olecranon is in contact with the head 23 of the excitor 13. While the forearm is in the upright position, the upper arm 3 is moved to a position where the back of the hand is situated. The hand of the subject is tied with the band member 11 secured to the upper arm 3 of the apparatus so that the back of the subject's hand makes the closest possible contact with the fixing plate 8 on the upper arm 3. Then, the upper arm 3 is gradually raised by rotating the handle 6 to lift the forearm slightly across the resting plate 19 and maintain it suspended in the air. It has been found that the subject's ulna can be effectively vibrated with reduced interferences by other bones, muscles, etc. if vibratory motion is applied in this state to the olecranon of the subject by the movable head 23 of the excitor 13.

The resonant frequency of the ulna can be measured, for example, by the method described in a Japanese-language publication "Bone Metabolism," Vol. 12, pages 317–323 (published in March 1979 by Kagaku Hyoronsha, Japan) after attaching a transducer to the capitulum ulnae part (see FIG. 1) of the wrist of the forearm mounted on the apparatus and if required also to the movable head of the excitor.

One specific example of the transducer which can be used in the measurement of resonant frequencies is shown in FIG. 7. In FIG. 7, the transducer shown at 40 consists of a protective casing 41 made of a plastic material, a metallic material, etc. and a ring member 42 made of a plastic material, a metallic material, etc. placed in the casing 41. At one end of the ring member 42 is stretched a piezoelectric film 45 having electrodes 43 and 44 of an electrically conductive thin film, such as a vacuum-deposited aluminum layer, bonded to both its surfaces. The outside surface of the electrode 44 may be covered with a protective film 46.

The piezoelectric film may be any piezoelectric film which acts as a transducer for converting mechanical vibration into an electrical signal. Preferably, for matching with the mechanical impedance of a living body, it should be an electret of a piezoelectric material such as polyvinylidene fluoride, or an electret of a composite of a polymer such as a polyamide, polyvinylidene fluoride or polyacetal resin with a piezoelectric ceramics.

Figure 8:
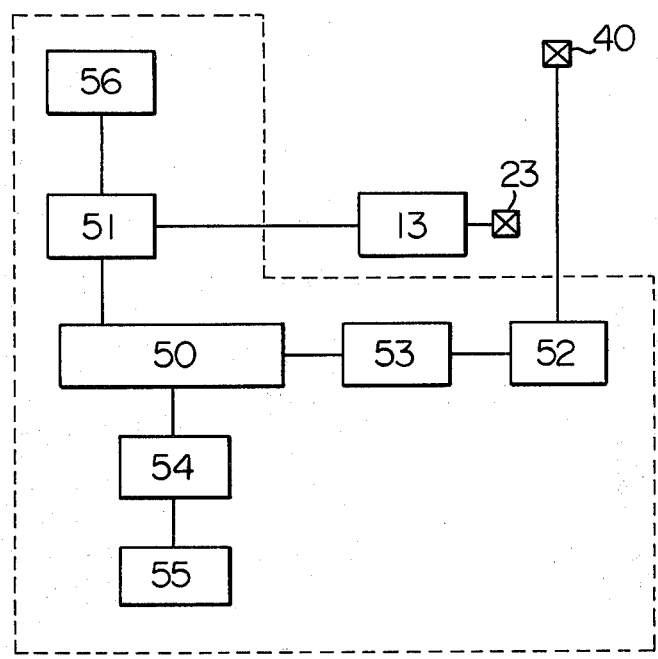
FIG. 8 is a block diagram of an electrical circuit used in the measurement of the resonant frequency of the ulna.

The resonant frequency of the ulna *in vivo* sensed by the transducer can be detected, for example, by using the electric circuit shown by the block diagram of FIG. 8.

A digital signal which varies in value from 100 to 1000 at one millisecond intervals is sent from a computing section 50 to an oscillator 51. In the oscillator 51, the digital signal is converted to the sine wave of the corresponding frequency, and is transmitted to the excitor 13 where it is converted to a mechanical force to vibrate the head 23. The vibration is thus propagated to the ulna and sensed by the transducer 40 provided in contact with the capitulum ulnae part of the wrist. The transducer 40 then converts the transmitted mechanical force to an analog electrical signal. The electrical signal is then sent to an amplifier 52 and converted to a digital signal by an A/D converter 53. The digital signal is sent to the computing section 50 and stored as a value corresponding to the transmitted digital signal.

The stored digital signal is converted to an analog electrical signal by a D/A converter 54 and sent to an oscilloscope 55 where it is displayed as a graph showing the applied frequency on the abscissa and the intensity of the received signal on the ordinate. Simultaneously, the frequency which gives the maximum amplitude (the resonant frequency) is read by the computing section 50 and digitally displayed on a display section 56 connected to the oscillator 51.

In the actual measurement of the resonant frequencies, this operation is repeated several times, and the average value of the intensities of the received signals corresponding to the respective frequencies on the graphs is displayed on the oscilloscope 55 as another graph. At the same time, the resonant frequency is digitally displayed at the display section 56. By reading this value, the condition of the bone of the subject can be diagnosed.

What is claimed is:

1. An apparatus for vibrating an ulna in vivo, comprising:
    a base stand;
    a main post provided upright on said base stand;
    a horizontally extending upper arm secured to an upper part of said main post for vertical movement;
    a plate means for fixing the back of a hand, said plate means being secured to an end of said upper arm for free movement at an arbitrary angle of inclination with respect to said upper arm, and having a band member which holds said hand onto said plate means so as to bring said back of said hand into closest possible contact with a surface of said plate means and to lift an antebrachium and maintain it suspended in the air;
    a lower arm means secured for vertical movement to a lower part of said main post and extending in the same horizontal direction as said upper arm;
    an excitor means mounted on the lower arm for sliding movement in the axial direction of said lower arm and in a horizontal direction perpendicular thereto, said excitor having a movable head which projects horizontally so as to abut against an olecranon in the axial direction of said lower arm; and
    a brachium resting plate fixed ahead of said excitor;
    wherein said ulna is vibrated by the excitor while its ends are kept free.

2. The apparatus of claim 1 wherein said excitor means is adapted to be turned up and down.

3. The apparatus of claim 1 wherein castors are secured to said base stand.

4. The apparatus of claim 1, wherein said excitor means is adapted to produce an output in the range of from 0.5 to 20 kgf.

5. The apparatus of claim 1, wherein guide plates are provided upright on both sides of said brachium resting plate as antebrachium holding means, and air bags are provided inwardly of said guide plates.

6. The apparatus of claim 1, wherein said brachium resting plate means is fixed to said base stand.

7. The apparatus of claim 1, wherein said brachium resting plate means is mounted on said lower arm means and at least an upper surface portion of said brachium resting plate means is made of a soft material.

8. The apparatus of claims 6 or 7, wherein antebrachium holding members are provided upright on both sides of said brachium resting plate means.

* * * * *